United States Patent [19]

Mori et al.

[11] 4,303,883
[45] Dec. 1, 1981

[54] APPARATUS FOR DETECTING THE CENTER OF A WELDED SEAM IN ACCORDANCE WITH FUNDAMENTAL HARMONIC COMPONENT SUPPRESSION

[75] Inventors: Toshihiro Mori; Seigo Ando; Hironobu Akuzawa, all of Yokohama, Japan

[73] Assignee: Nippon Kokan Kabushiki Kaisha, Tokyo, Japan

[21] Appl. No.: 57,029

[22] Filed: Jul. 12, 1979

[30] Foreign Application Priority Data

Jul. 17, 1978 [JP] Japan .................................. 53-86123

[51] Int. Cl.³ ....................... G01B 7/14; G01R 33/12; G01N 27/72
[52] U.S. Cl. .................................... 324/208; 324/243
[58] Field of Search ............... 324/207, 208, 225, 233, 324/234, 239-243, 260, 262

[56] References Cited

U.S. PATENT DOCUMENTS

| | | | |
|---|---|---|---|
| 3,359,486 | 12/1967 | Brosious | 324/233 |
| 3,430,134 | 2/1969 | Flaherty | 324/243 |
| 3,617,874 | 11/1971 | Forster | 324/241 |
| 4,030,026 | 6/1977 | Payne | 324/239 |

Primary Examiner—Gerard R. Strecker
Assistant Examiner—Walter E. Snow
Attorney, Agent, or Firm—Fleit & Jacobson

[57] ABSTRACT

An apparatus first magnitizes a base metal with an alternating flux to cross the welded seam of the base metal and the resulting leakage flux from the welded seam is detected by at least one flux search element to generate an AC signal. The fundamental harmonic component corresponding to the magnetizing signal used for the alternating magnetization is eliminated from the AC signal and the resulting signal voltage is sampled at a fixed period corresponding to the period of the magnetizing signal, thus detecting the center position of the welded seam from the result of the sampling. The apparatus comprises a magnetizing coil arranged adjacent to the base metal for the alternating magnetization thereof, at least one flux search element disposed adjacent to the base metal for leakage flux detecting purposes, means for eliminating from the detected AC output signal of the element the fundamental harmonic component corresponding to the magnetizing signal used for the alternating magnetization and a sampling circuit for sampling the output signal voltage of the eliminating means at a predetermined period, whereby the relative positional relation between the flux search element and the center of the welded seam is determined in accordance with the polarity and the amplitude value of the output voltage of the sampling circuit.

6 Claims, 8 Drawing Figures

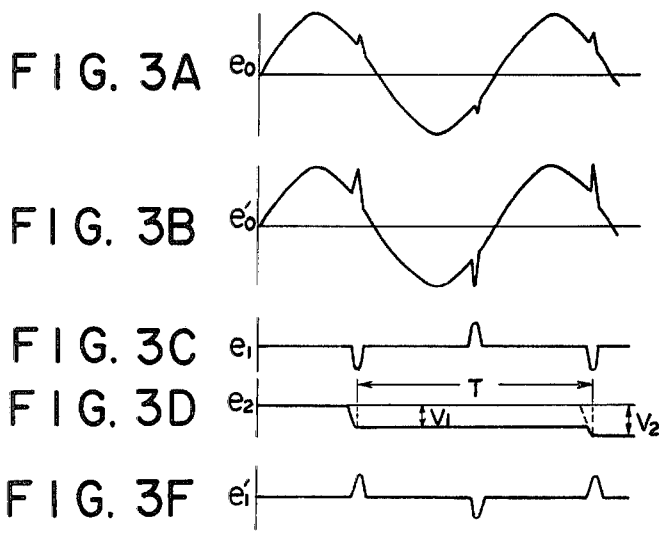
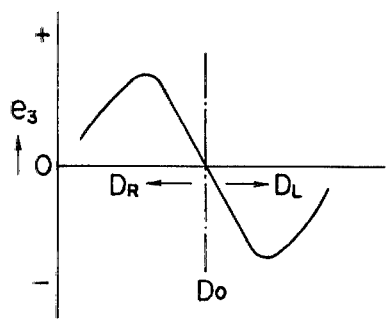

APPARATUS FOR DETECTING THE CENTER OF A WELDED SEAM IN ACCORDANCE WITH FUNDAMENTAL HARMONIC COMPONENT SUPPRESSION

BACKGROUND OF THE INVENTION

The present invention relates to apparatus wherein the leakage flux from the welded seam of a base metal magnetized with an alternating flux is detected to detect the center of the welded seam, and more particularly the invention relates to an apparatus for detecting the center of the welded seam of a steel material, such as the welded joint of an annealed electric welded pipe which is less different in material properties from the base metal portion.

To detect the center of the welded seam of a steel material is essential, as for example, for effecting the desired noncontact copying control of a flaw detector in the ultrasonic flaw detection of a welded joint. In the past, with the flaw detection of the welded joint of a welded steel pipe by means of an ultrasonic flaw detector, for example, in order that the probe of the flaw detector may be controlled in a noncontact manner to follow along the center of the welded seam, the difference in properties, particularly magnetic properties between the base metal portion and the welded joint of the steel pipe is detected by the eddy-current detecting probe and a signal detecting the position of the welded seam is generated for copying control purposes. The use of such eddy-current detecting probe has the disadvantage of deteriorated detection sensitivity due to the mere detection of the eddy current induced in the steel pipe by the probe coil and moreover, excepting the cases where there is any large difference in properties between the base metal portion and the welded joint, it is not possible to effectively detect the center of the welded seam of materials, such as an annealed electric welded pipe in which practically all such differences in properties have been eliminated.

SUMMARY OF THE INVENTION

It is a principal object of the invention to provide an apparatus which is capable of detecting with a high degree of accuracy the center of the welded seam of even such a base metal in which the difference in magnetic properties between the base metal portion and the welded joint is very small.

It is another object of the invention to provide such apparatus in which a base metal is magnetized with an alternating flux from a coil energized by commercial power supply and the resulting AC leakage flux from its welded seam is detected to thereby detect the center of the welded seam in a noncontact manner.

It is still another object of the invention to provide such apparatus in which variations in the center position of the welded seam of a base metal can be detected continuously along the lengthwise direction of the seam in terms of the relative positional relation between the center position and the leakage flux search means.

In accordance with the invention there is thus provided an apparatus for detecting the center of a welded seam comprising a pair of magnetizers which are preferably arranged on both sides of and adjacent to the welded seam of a steel material so as to apply an AC magnetic flux to the steel material to cross the welded seam, a leakage flux search element arranged between the pair of magnetizers and fixedly attached to associated the magnetizers in the vicinity of the welded seam so as to detect the leakage flux from the welded seam of the steel material AC magnetized by the magnetizers, and a detecting circuit whereby the fundamental harmonic component corresponding to the exciting voltage waveform used for the alternating magnetization is eliminated from the AC voltage induced in the leakage flux search element and the resulting signal voltage is sampled at a predetermined period, whereby the center position of the welded seam is detected in terms of the relative positional relation between it and the leakage flux search element in accordance with the polarity and voltage value of the sampled output generated from the detecting circuit.

The magnetizers and the leakage flux search element are integrally supported on a mount to form a detecting terminal, and consequently by for example moving the detecting terminal relative to a steel material along the lengthwise direction of its welded seam, it is possible to continuously detect the distance of the center line of the welded seam from the center line of the detecting terminal in the direction of travel thereof and the resulting detection output can be used as such for the purpose of copying control of a flaw detector or the like.

The sampling period is synchronized with the period of the exciting current for alternating magnetization, and the timing of the sampling is subjected to phase control to adjust in a manner that the sampled output is reduced to zero when the center of the welded seam aligns with the center or middle point of the leakage flux search element and that when the centers deviate to the left or right the sampled output assumes a positive or negative polarity voltage value corresponding to the amount of deviation.

Other objects, construction and functional effects of the invention will appear more apparent from the accompanying drawings showing the preferred embodiments of the invention.

BRIEF DESCRIPTION OF THE DRAWINGS

FIGS. 3A-3E are a diagram showing the waveform generated at various points in FIG. 2.

FIG. 4 is a graph showing a detection output characteristic of the detecting circuit.

DESCRIPTION OF THE PREFERRED EMBODIMENTS

Figure 1:
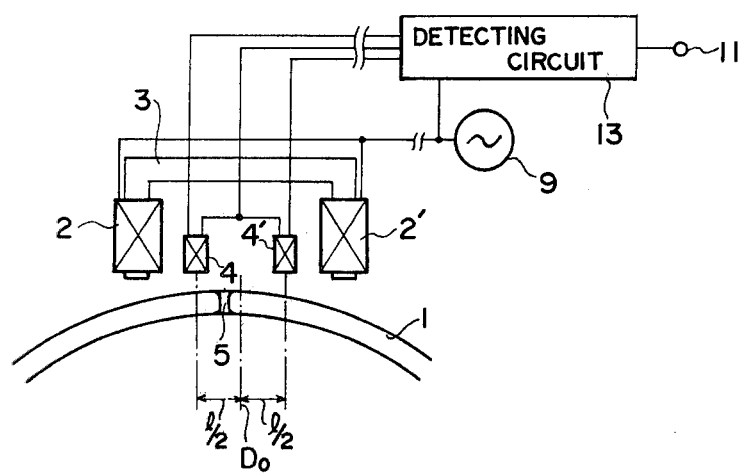
FIG. 1 is a block diagram showing the construction of an apparatus according to an embodiment of the invention.

Referring first to FIG. 1, numeral 1 designates a welded steel pipe as an example of steel product to be inspected, and a pair of magnetizing cells 2 and 2' are mounted on a solid yoke 3 so as to be positioned along the outer surface of the steel pipe 1 in the vicinity of a welded seam 5 located between the coils 2 and 2'. A pair of leakage flux search coils 4 and 4' are arranged between the magnetizing coils 2 and 2' on both sides of the seam 5, and the magnetizing coils 2 and 2' and the search coils 4 and 4' are mechanically integrally fixed in place so as to prevent any variation in their relative positions.

An alternating current of a fixed frequency is applied to the magnetizing coils 2 and 2' from an AC power source 9 so that the AC magnetic flux produced from the magnetizing coils 2 and 2' are applied to the steel pipe 1 to cross the seam 5 and the steel pipe 1 is magnetized with the alternating flux at the fixed frequency. Even if it is so small, the welded joint portion is different in magnetic properties from the base metal portion of the steel pipe 1 and consequently the leakage flux from the welded seam 5 of the AC magnetized steel pipe 1 differs in flux density from the flux from the coils 2 and 2'. The leakage flux is detected by the search coils 4 and 4' so that a voltage is induced in each of the coils 4 and 4' and the induced voltages are processed by a detecting circuit 13 which in turn generates a detection output as its output terminal 11.

Figure 2:
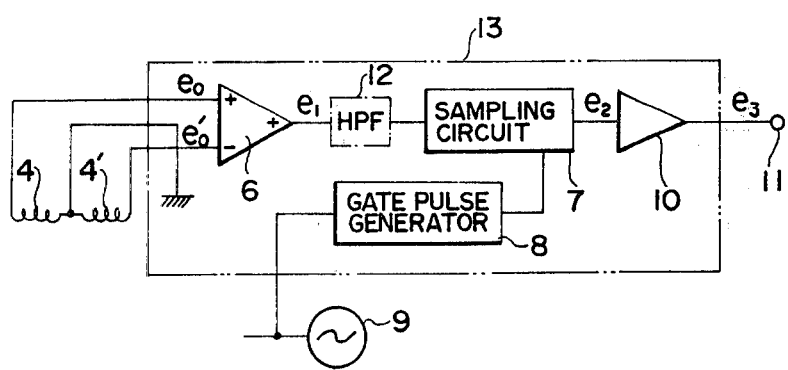
FIG. 2 is a block diagram showing an embodiment of the detecting circuit shown in FIG. 1.

As shown in FIG. 2, the detecting circuit 13 comprises a differential amplifier 6 for differently amplifying the output voltages of the coils 4 and 4', a sampling circuit 7 for sampling the output of the differential amplifier 6 at a predetermined period to generate a sampled and held output, a gate pulse generator 8 responsive to the AC voltage signal from the AC power source 9 to apply gate pulses to the sampling circuit 7 at the predetermined sampling period and a DC amplifier 10 for amplifying the sampled and held output with a predetermined gain.

With the construction described above, when the magnetizing coils 2 and 2' are energized by the alternating current of a predetermined frequency supplied thereto from the AC power source 9 comprising a commercial power supply or the like, the greater part of the AC flux having the predetermined frequency and generated from the magnetizing coils 2 and 2', respectively, is transmitted through the wall thickness of the steel pipe 1 to cross the welded seam 5 and the thus transmitted magnetic flux causes a pulse-like leakage flux of the said frequency to leak from the portion of the welded seam 5. The pulse-like magnetic flux leaked from the seam 5 causes in each of the search coils 4 and 4' an induced voltage containing a pulse-like component and the waveforms of the induced voltages generated in the coils 4 and 4' are respectively shown at $e_o$ and $e'_o$ in (A) and (B) of FIG. 3. In other words, the voltage $e_o$ induced in the coil 4 and the voltage $e'_o$ induced in the coil 4' respectively has a waveform including as the fundamental harmonic component the same sinusoidal wave as the AC exciting voltage used for the alternating magentization and the pulse-wave component resulting from the leakage flux peculiar to the welded seam 5 and superimposed on the fundamental harmonic components, and the voltages $e_o$ and $e'_o$ are of the same phase.

For instance, where the welded seam 5 is deviated toward the coil 4 from the middle point $D_o$ between the pair of search coils 4 and 4' of a spatial dimension l as shown in FIG. 1, the pulse wave in the signal voltage $e'_o$ generated from the coil 4' has a peak value which is greater than that of the pulse wave in the signal voltage $e_o$ from the coil 4 as shown in (A) and (B) of FIG. 3. As shown in FIG. 2, the signal voltages $e_o$ and $e'_o$ are applied to the differential amplifier 6 where the fundamental harmonic components of the same phase are eliminated and consequently a pulse signal $e_1$ corresponding to the difference between the two pulse waves is generated from the amplifier 6 as shown in (C) of FIG. 3. The signal voltage $e_1$ is applied to the sampling circuit 7 so that the signal voltage $e_1$ is sampled at a predetermined period T by the gate pulses applied from the gate pulse generator 8, held at the voltage existing at the time of the sampling and then generated as a signal voltage $e_2$ as shown in (D) of FIG. 3. The gate pulse is synchronized with the exciting current applied to the magnetizing coils 2 and 2' and the period T is equal to the output period of the AC power source 9. As shown in (D) of FIG. 3, the signal voltage $e_2$ represents the output pulse signal $e_1$ of the amplifier 6 which was sampled and held at voltages $V_1$ and $V_2$ at the predetermined period T, and the resulting voltage is amplified by the DC amplifier 10 and then delivered as a detection output signal $e_3$ to the output of terminal 11.

On the other hand, when the welded seam 5 is deviated toward the coil 4', the output voltage of the amplifier 6 results, as shown in (E) of FIG. 3, in a pulse signal $e'_1$ of the opposite polarity to that shown in (C) of FIG. 3, and if the signal $e'_1$ is sampled and held by the same sampling timing, an output which is opposite in polarity to that shown in (D) of FIG. 3 will be generated.

As a result, the voltage value of the output signal $e_3$ corresponding to the instantaneous value obtained by sampling the output of the differential amplifier 6 at the period T of the power source 9, has a positive or negative polarity depending on whether the center of the welded seam 5 is in a right position $D_R$ or left position $D_L$ with respect to the center or middle point $D_o$ between the search coils 4 and 4'. If the timing of sampling is adjusted by subjecting the gate pulse generator 8 to phase control in such a manner that the output voltage $e_3$ become exactly zero V when the center of the seam 5 is an alignment with the middle point $D_O$ between the coils 4 and 4', it is possible to determine the center of the welded seam 5 in accordance with the relative positional relation between it and the coils 4 and 4' when the output voltage $e_3$ becomes zero V.

On the other hand, if the magnetizing coils 2 and 2' and the search coils 4 and 4' which are integral with the former are shifted by a servomechanism in such a manner that the output voltage $e_3$ always becomes zero V, it is possible to follow the welded seam 5 along the lengthwise direction thereof.

While, in the above-described embodiment, the flux search means comprises the search coils 4 and 4', the similar effect may be obtained with a single search coil or alternatively the search coils 4 and 4' may be replaced with magnetic sensors such as Hall devices or magnetic sensitive diodes. Further, the output voltage $e_1$ of the differential amplifier 6 may be passed through a high-pass filter 12 as shown by the dotted line in FIG. 2 so as to eliminate the leakage component of the fundamental harmonic. Where only the single search coil is used, the fundamental harmonic component will be eliminated only by the high-pass filter.

While, in the embodiment described above, the magnetizing method used is the Magnetic Pole Method (test piece is placed between two poles of electromagnet JIS Code M) stated on JIS G0565-1974, any other method such as the End Contact Method (magnetizing current is send to the test piece in the direction of the piece axis JIS code EA) or the Bar Method (magnetizing current is send to the conductor passing through the hole of the test piece JIS Code B) may be used.

The apparatus of the invention for detecting the center of a welded seam can be used in such applications as the rotational positioning of the welded seam of welded pipes, the determination of the center of sheet plate welded joints and detection of the passage thereof or the flaw detection including the detection of cracks in steel products.

What is claimed is:

1. An apparatus for detecting the center of a welded seam of an AC magnetized welded steel material by detecting leakage flux from said welded seam comprising:
   an AC power source having an output,
   magnetizing means connected to said AC power source for AC magnetizing said steel material by magnetic flux crossing said welded seam,
   leakage flux search means fixedly mounted integral with said magnetizing means for detecting leakage flux from said welded seam so as to provide an induced voltage corresponding to a change in said leakage flux, said induced voltage comprising a fundamental harmonic corresponding to an excitation voltage waveform used for said AC magnetization and a pulse like component corresponding to said welded seam, and
   detecting means responsive to said induced voltage from said leakage flux search means for detecting a center position of said welded seam in terms of a relative positional relation between said center position and said leakage flux search means;
   wherein said detecting means comprises first means for eliminating from said induced voltage the fundamental harmonic component corresponding to the excitation voltage waveform used for said AC magnetization while leaving at least the pulse-like component, second means for producing from said output of said AC power source a gate pulse signal having a predetermined period for sampling, and third means responsive to said gate signal for sampling at said predetermined period, said induced voltage having said fundamental harmonic component eliminated therefrom and having at least said pulse-like component, whereby in accordance with the polarity and voltage value of a sampled output from said third means the center position of said welded seam is detected in terms of a relative positional relation between said center position and said search means.

2. An apparatus according to claim 1, wherein said leakage flux search means comprises a pair of magnetic flux detecting elements arranged opposite to each other on both sides of said welded seam for inducing voltages, and wherein said first means includes a differential amplifier for differentially amplifying said induced voltages of said detecting elements.

3. An apparatus according to claim 1, further comprising a high-pass filter connected between said first means and third means for further suppressing said fundamental harmonic component.

4. An apparatus according to claim 1, wherein said magnetizing means comprises a pair of magnetizers arranged on both sides of said leakage flux search means.

5. An apparatus according to claim 1, wherein said first means produces an output voltage, and said third means includes a sampling circuit for sampling said output voltage of said first means each time a gate pulse signal is applied and for generating an output holding a sampled voltage until a next gate pulse signal arrives.

6. An apparatus according to claim 1, wherein said gate pulse signal has a phase, and said second means includes a gate pulse generator for changing the phase of said gate pulse signal with respect to the output of said AC power source while maintaining the period of said gate pulse signal constant.

* * * * *